US012642603B2

(12) United States Patent
Lutz et al.

(10) Patent No.: US 12,642,603 B2
(45) Date of Patent: Jun. 2, 2026

(54) REAL-TIME SUPPORT SYSTEM FOR PERFORMING AT LEAST ONE BONE TUNNEL BY ARTHROSCOPY

(71) Applicant: AREAS, Lyons (FR)

(72) Inventors: Christian Lutz, Eschau (FR); Bertrand Sonnery-Cottet, Lyons (FR); Pierre Imbert, Frejus (FR); Yvon Gautier, Grenoble (FR); Romain Benoit, Brié et Angonne (FR)

(73) Assignee: AREAS, Grenoble (FR)

( * ) Notice: Subject to any disclaimer, the term of this patent is extended or adjusted under 35 U.S.C. 154(b) by 0 days.

(21) Appl. No.: 19/122,814

(22) PCT Filed: Oct. 23, 2023

(86) PCT No.: PCT/FR2023/051659
§ 371 (c)(1),
(2) Date: Apr. 21, 2025

(87) PCT Pub. No.: WO2024/089352
PCT Pub. Date: May 2, 2024

(65) Prior Publication Data
US 2026/0124000 A1 May 7, 2026

(30) Foreign Application Priority Data
Oct. 24, 2022 (FR) ...................................... 2211023

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 34/30* (2016.02); *G06T 7/0012* (2013.01);
(Continued)

(58) Field of Classification Search
CPC ......... A61B 34/20; A61B 34/10; A61B 34/30; A61B 2034/102; A61B 2034/105; G06T 2207/30008
See application file for complete search history.

(56) References Cited

U.S. PATENT DOCUMENTS

| 7,123,255 | B2 | 10/2006 | Trousett et al. |
| 10,499,996 | B2 | 12/2019 | de Almeida Barreto |
(Continued)

FOREIGN PATENT DOCUMENTS

| DE | 102020117188 A1 | 12/2021 |
| EP | 3375399 A2 | 9/2018 |
(Continued)

OTHER PUBLICATIONS

Banach et al., "Visual Localisation for Knee Arthroscopy", International Journal of Computer Assisted Radiology and Surgery, Springer, DE, vol. 16, No. 12, Jul. 4, 2021 (Jul. 4, 2021), pp. 2137-2145, [retrieved on Jul. 4, 2021], DOI: 10.1007/S11548-021-02444-8, ISSN: 1864-6410, XP037628538.
(Continued)

*Primary Examiner* — Jason M Ip
(74) *Attorney, Agent, or Firm* — Perkins Coie LLP

(57) ABSTRACT

A system for assisting in real time in the production of at least one bone tunnel by arthroscopy in a joint of a patient, including an imaging device able to acquire two-dimensional images of portions of the joint of the patient, a first monitoring device and a programmable device.

15 Claims, 9 Drawing Sheets

(51) Int. Cl.

| | | |
|---|---|---|
| *A61B 34/30* | (2016.01) | |
| *G06T 7/00* | (2017.01) | |
| *G06T 7/33* | (2017.01) | |
| *G06T 7/73* | (2017.01) | |
| *G06T 19/00* | (2011.01) | |

(52) U.S. Cl.
CPC ................ *G06T 7/344* (2017.01); *G06T 7/75* (2017.01); *G06T 19/006* (2013.01); *A61B 2034/102* (2016.02); *A61B 2034/105* (2016.02); *G06T 2207/30008* (2013.01); *G06T 2207/30196* (2013.01); *G06T 2210/41* (2013.01)

(56) References Cited

U.S. PATENT DOCUMENTS

| | | | |
|---|---|---|---|
| 11,730,342 | B2 | 8/2023 | Ries et al. |
| 12,064,187 | B2 | 8/2024 | Bleunven et al. |
| 2003/0210812 | A1 | 11/2003 | Khamene et al. |
| 2006/0161052 | A1 | 7/2006 | Columbet et al. |
| 2013/0211232 | A1 | 8/2013 | Murphy et al. |
| 2016/0338776 | A1 | 11/2016 | Jaramaz et al. |
| 2018/0174311 | A1 | 6/2018 | Kluckner et al. |
| 2021/0259774 | A1 | 8/2021 | Fouts et al. |
| 2021/0322148 | A1 | 10/2021 | Mitra et al. |
| 2022/0296302 | A1 | 9/2022 | Bleunven et al. |
| 2023/0074630 | A1 | 3/2023 | Knopf |
| 2023/0200928 | A1 | 6/2023 | Quist et al. |
| 2023/0363831 | A1 | 11/2023 | Jaramaz et al. |
| 2024/0358224 | A1* | 10/2024 | Quist ................ A61B 1/00057 |
| 2025/0049448 | A1 | 2/2025 | Quist et al. |

FOREIGN PATENT DOCUMENTS

| | | | |
|---|---|---|---|
| EP | 3922204 | A1 | 12/2021 |
| EP | 3936075 | A2 | 1/2022 |
| FR | 2920565 | B1 | 12/2009 |
| WO | 2021257672 | A1 | 12/2021 |
| WO | 2022195303 | A1 | 9/2022 |
| WO | 2024089352 | A1 | 5/2024 |
| WO | 2024213641 | A1 | 10/2024 |
| WO | 2025068248 | A1 | 4/2025 |
| WO | 2025071921 | A1 | 4/2025 |

OTHER PUBLICATIONS

Barratt DC, Penney GP, Chan CS, Slomczykowski M, Carter TJ, Edwards PJ, Hawkes DJ. Self-Calibrating 3D-Ultrasound-Based Bone Registration for Minimally Invasive Orthopedic Surgery, IEEE Transactions on Medical Imaging. Mar. 2006;25(3).

Cabitza F, Locoro A, Banfi G. Machine learning in orthopedics: a literature review. Frontiers in bioengineering and biotechnology. Jun. 27, 2018;6:75.

Chen et al., "SLAM Endoscopy enhanced by adversarial depth prediction", arxiv.org, Cornell University Library, 201 Olin Library Cornell University Ithaca, NY 14853, Jun. 29, 2019 (Jun. 29, 2019), XP081379828.

Cilla M, Borgiani E, Marinez J, Duda GN, Checa S. Machine learning techniques for the optimization of joint replacements: Application to a short-stem hip implant. Plos one. Sep. 5, 2017;12(9):e0183755.

Dhaher YY, Salehghaffari S, Adouni M. Anterior laxity, graft-tunnel interaction and surgical design variations during anterior cruciate ligament reconstruction: A probabilistoc simulation of the surgery. Journal of biomechanics. Sep. 6, 2016;43(13):3009-16.

Kumar et al., "DepthNet: A Recurrent Neural Network Architecture for Monocular Depth Prediction", 2018 IEEE/CVF Conference on Computer Vision and Pattern Recognition Workshops (CVPRW), IEEE, Jun. 18, 2018 (Jun. 18, 2018), pp. 396-404, DOI: 10.1109/ CVPRW.2018.00066, XP033475663.

Musahl V, Plakseychuk A, VanScyoc A, Sasaki T, Debski RE, Mcmahon PJ, Fu FH. Varying femoral tunnels between the anatomical footprint and isometric positions: effect on kinematics of the anterior cruciate ligament-reconstructed knee. The American journal of sports medicine. May 2005;33(5):712-8.

Osti M, Krawinkel A, Ostermann M, Hoffelner T, Benedetto KP, Femoral and tibial graft tunnel parameters after transtibial, anteromedial portal, and outside-in single-bundle anterior cruciate ligament reconstruction. The American journal of sports medicine. Sep. 2015; 43(9):2250-8.

Raposo et al., "Video-based computer navigation in knee arthroscopy for patient-specific ACL reconstruction", International Journal of Computer Assisted Radiology and Surgery, https://doi.org//10. 1007/s11548-019-02021-0, Received: Feb. 7, 2019, Accepted: Jun. 24, 2019, Published online: Jun. 29, 2019, 11 pages.

Extended European Search Report, EP Application No. 25306486.9, mail date: Mar. 5, 2026, 7 pages.

File History of related U.S. Appl. No. 63/839,639, filed Jul. 7, 2025.

File History and the references cited therein of related U.S. Appl. No. 19/331,275, filed Sep. 17, 2025.

File History of related U.S. Appl. No. 63/819,028, filed Jun. 6, 2025.

File History of related U.S. Appl. No. 63/819,052, filed Jun. 6, 2025.

File History of related U.S. Appl. No. 63/844,973, filed Jul. 16, 2025.

File History of related U.S. Appl. No. 63/844,341, filed Jul. 15, 2025.

File History of related U.S. Appl. No. 63/884,097, filed Sep. 18, 2025.

International Search Report Translation and Written Opinion, I.A. No. PCT/FR2023/051659, ISA/EP, mail date: Jan. 26, 2024, 6 pages.

\* cited by examiner

REAL-TIME SUPPORT SYSTEM FOR PERFORMING AT LEAST ONE BONE TUNNEL BY ARTHROSCOPY

FIELD

The present invention relates to assistance in surgery by arthroscopy. More particularly, the invention relates to a system for real-time assistance in producing at least one bone tunnel in a joint of a patient during surgery.

BACKGROUND

Ligament reconstruction surgeries of the knee are operations that consist in replacing one or more ligaments of the knee joint, connecting the femur to the tibia with a strip of tendinous tissue, which will constitute the neoligament, taken from the patient (autografting) or, more rarely, taken post-mortem from donors (allografting). The surgeon will then produce a bone tunnel in the femur and a bone tunnel in the tibia and position these tunnels in the insertions of the injured ligament, and then pass the graft into these tunnels before securing it.

Two major types of ligaments can be distinguished. First of all, there are intra-articular ligaments that connect the femur to the tibia by passing through the articular space of the knee, a space defined and delimited by the articular capsule. The other category of ligament relates to extra-articular ligaments, located at the periphery of the knee and that connect the knee to the tibia without passing through the articular space.

Intra-articular ligaments are ligaments that are easily identifiable and individualizable. In particular they can be observed by means of an arthroscope, i.e. by introducing a mini camera into the articular space through a mini incision (arthroscopic door).

In contrast, extra-articular ligaments are located at the periphery of the joint, and are "bonded" to the articular capsule. These ligaments are therefore not observable under arthroscopy and are difficult to identify and individualise. During surgery, locating these extra-articular ligaments and in particular the bone insertions thereof to reconstruct them requires the making of wide incisions and a lengthy dissection step. Some extra-articular ligaments that are very fine and bonded to the articular capsule, such as for example the anterolateral ligament or the medial femoral-patellar ligament, are almost not identifiable by dissection.

Placement of bone tunnels in the native insertion of the ligaments is therefore not always possible for certain structures and in certain cases when such insertion has been altered during trauma (such as for example the femoral insertion of the anterior cruciate ligament —ACL, which is often injured during rupture of the latter).

Moreover, it is often necessary, during the same operation, to position several bone tunnels. Indeed, medical imaging studies of the last years have made it possible to demonstrate that isolated rupture of the anterior cruciate ligament (ACL) is in fact rare and in the majority of cases is accompanied by a lesion of a very specific extra-articular ligament, the anterolateral ligament (ALL). Reconstruction of the ACL and of the ALL is today indicated for the majority of patients. Thus, in rare cases of serious sprain of the knee, several intra-and extra-articular ligaments are injured and must be reconstructed. Currently, mechanical sights help in the positioning of bone tunnels during a surgical operation of the knee for reconstructing intra-articular ligaments. The principle is based on the placing of a guide pin on which the tunnel will next be pierced by means of a cannulated bit.

In a first so-called 'IN OUT' sighting technique, the femoral pin is placed from the inside towards the outside of the joint. In this technique, the exiting of the tunnel on the external part of the bone is not controlled and is susceptible to cause iatrogenic lesions. Moreover, this technique does not allow the positioning of the grafts for reconstructing the extra-articular ligaments such as the anterolateral ligament.

In a second so-called 'OUT IN' sighting technique, the pin is placed from the outside towards the inside of the joint. This technique makes it possible to make sightings with the knee at 90 degrees of bending. For these OUT INsights, the point of entry on the outside of the bone is made percutaneously (i.e. through the skin) and the zone is selected after palpation of the bone relief (here, the lateral epicondyle). Positioning this entry point by palpation therefore remains unreliable and unreproducible.

There are moreover computer-aided sighting systems providing supplementary information to the surgeon by using in real time an imaging technique, such as radioscopy, during the operation and projecting points acquired by means of a sensor onto the knee of the patient in real time on this imaging. However, radioscopy during surgery is an irradiant process. Also, this sighting system only takes into account the positioning of the intra-articular tunnels and allows neither a precise positioning of the extra-articular orifice nor achieving the precise positioning of the extra-articular grafts.

There is thus in the prior art no system making it possible to meet the new requirements of ligament reconstructions of the knee, i.e. a system compatible and consistent with arthroscopy, not giving rise to any significant additional operating time or significant extra cost, precise and adapted to reconstructions of two ligaments at the same time, for example an inter-articular ligament and an extra-articular ligament.

SUMMARY

The invention relates to a system assisting the production of at least one bone tunnel by arthroscopy in a joint of a patient using a surgical piercing instrument, comprising an imaging device or a measuring device, a monitoring device and a programmable device, said programmable device being adapted to:

obtain a preoperative three-dimensional anatomical model specific to the patient, said model comprising a representation of at least one portion of interest of the joint of the patient and a representation of anatomical structures of interest, acquire monitoring information of the current position and orientation of the surgical piercing instrument during a manipulation of said surgical piercing instrument by an operator using the monitoring device;

determine a peroperative partial three-dimensional anatomical model comprising a representation of the at least one portion of interest of the joint, by:

acquiring, using the imaging device, a stream of peroperative two-dimensional images comprising said at least one portion of interest of the joint, and acquiring monitoring information of the current position and orientation of the imaging device using the monitoring device; wherein said peroperative partial three-dimensional anatomical model is obtained from the stream of peroperative bidimensional images and said monitoring information of the current position and orientation, or acquiring, using the measuring device, a cloud of points representative of the at least one portion of interest of the joint, and acquiring monitoring information of the current position and orientation of said measuring device; wherein said peroperative partial three-dimensional anatomical model is obtained from said cloud of points;

register the preoperative three-dimensional anatomical model on the peroperative partial three-dimensional anatomical model;

calculate, on the basis of information obtained with the registering of the preoperative three-dimensional anatomical model, and of the current position and orientation of the surgical piercing instrument:

a current zone of localization, in a current peroperative two-dimensional image, of a piercing end of the surgical piercing instrument, a first projection comprising a current estimation of a zone of localization of a first orifice of a bone tunnel to be produced, a second projection comprising a current estimation of a zone of localization of a second orifice of a bone tunnel to be produced.

In one embodiment, the invention relates to a system assisting in real time in the production of at least one bone tunnel by arthroscopy in a joint of a patient using a surgical piercing instrument, comprising an imaging device able to acquire two-dimensional images of portions of the joint of the patient, a monitoring device and a programmable device, said programmable device being adapted to:

obtain a preoperative three-dimensional anatomical model specific to the patient, said model comprising a representation of at least one portion of interest of the joint of the patient and a representation of anatomical structures of interest, acquire, using the imaging device, a stream of peroperative two-dimensional images, said peroperative two-dimensional images comprising said portion of interest of the joint, and acquire monitoring information of the current position and orientation of the imaging device using the monitoring device;

acquire monitoring information of the current position and orientation of the surgical piercing instrument during a manipulation of the surgical piercing instrument by an operator using the monitoring device;

determine a peroperative partial three-dimensional anatomical model from the stream of peroperative two-dimensional images and/or from a cloud of points representative of the portion of interest of the joint obtained using a measuring device;

register the preoperative three-dimensional anatomical model on the peroperative partial three-dimensional anatomical model;

calculate, on the basis of information obtained with the registering of the preoperative three-dimensional anatomical model, and of the current position and orientation of the surgical piercing instrument:

a current zone of localization, in a current peroperative two-dimensional image, of a piercing end of the surgical piercing instrument, a first projection comprising a current estimation of a zone of localization of a first orifice of a bone tunnel to be produced, a second projection comprising a current estimation of a zone of localization of a second orifice of a bone tunnel to be produced.

Thanks to the invention, a surgeon performing an operation requiring the production of at least one bone tunnel can know in real time, according to the position and orientation of their surgical piercing instrument, the corresponding positions of the entry zone and of the exit zone of the bone tunnel to be produced. The surgeon can thus adjust the position and the orientation of the surgical piercing instrument in order to target a precise entry zone or exit zone of the bone tunnel.

In one embodiment, the registration of the preoperative three-dimensional anatomical model on the peroperative partial three-dimensional anatomical model is obtained via a 3D/3D registration technique.

In one embodiment, said peroperative partial three-dimensional anatomical model comprising a representation of the portion of interest of the joint.

In one embodiment, the programmable device is further configured to calculate:

in the first projection, first projections of a first part of the representation of the anatomical structures of interest during an operation phase, and/or in the second projection, second projections of a second part of the representation of the anatomical structures of interest.

Thus, it is possible for a surgeon, during an operation, to know the position in real time of the entry zone and of the exit zone of the bone tunnel to be produced with respect to the anatomical structures of interest and to adjust the position and/or the orientation of their surgical piercing instrument so as to position the entry zone and the exit zone of the bone tunnel with respect to these anatomical structures of interest so as not to damage certain of these anatomical structures of interest during the piercing of the bone tunnel. By anatomical structures of interest, it is meant anatomical references allowing to help during the operation in positioning their working instruments such as the surgical piercing instrument to produce a bone tunnel. For example, the anatomical structures of interest comprise bone contours of the femur, of the tibia, of the patella and of the head of the fibula, a representation of the cartilaginous contours of the femur and of the tibia, a complete or partial representation of the anterior cruciate ligament, of the posterior cruciate ligament, of the external lateral ligament, of the internal lateral ligament and of the femoropatellar ligament.

Furthermore, the anatomical structures of interest comprise bone reliefs, cartilaginous boundaries, and tendinous or ligamentous structures. In other words, the anatomical structures of interest comprise anatomical references and any so-called noble structure not to be damaged during an operation.

In one embodiment, the real-time assistance system further comprises a display unit and further adapted to display on the display unit:

a superimposition of the current peroperative two-dimensional image and of the current localization zone of the piercing end of the surgical piercing instrument, a first superimposition of the first projection and of the first projections of the first part of the representation of the anatomical structures of interest, a second superimposition of the second projection and of the second projections of the second part of the representation of the anatomical structures of interest.

Thus a surgeon, during operation, can view in real time the position of the entry zone and of the exit zone and adjust the position/orientation of their surgical piercing instrument so as to avoid any damage to anatomical structures of interest.

In one embodiment, the real-time assistance system is further adapted to, before obtaining the preoperative three-dimensional anatomical model, obtain and store a plurality of preoperative two-dimensional and/or three-dimensional images comprising the portion of interest of the joint.

Operations on the knee often being previously preceded by examinations using the magnetic resonance imaging technique, such as conventionally in the health run of a patient, the results of such examinations can advantageously be used to generate the three-dimensional model.

In one embodiment, the real-time assistance system is further adapted to calculate an intersection between the current estimation of the localization zone of the first orifice, respectively of the second orifice, current with the first projections of the first part, respectively the second projections of the second part of the representation of the anatomical structures of interest.

Thus, the real-time assistance system allows to detect, according to the position and the orientation of the surgical piercing instrument, every possibility of intersection of the corresponding bone tunnel with this position and this orientation.

In one embodiment, the real-time assistance system is further adapted, when the intersection with the first, respectively second, projections comprises a portion of the first projections of the first part of the representation of the anatomical structures of interest or a portion of the second projections of the second part of the representation of the anatomical structures of interest, to display an information message on the first, respectively, the second superimposition.

The display of an information message allows to help the surgeon in real time to adjust the current position and orientation of their surgical piercing instrument, and therefore to reduce the risk of error during the surgery.

In one embodiment, the real-time assistance system is further adapted to, after a production of a first bone tunnel in the joint of the patient, calculate on the first, respectively second, current projection a first, respectively second, pattern representative of the localization of the first bone tunnel. In other words, after the production of a first bone tunnel in the joint of the patient, the system is further configured to calculate a three-dimensional representation of the first bone tunnel and to calculate, on the first, respectively second, current projection, a first, respectively second, two-dimensional view of said three-dimensional representation of the first bone tunnel.

Thus, the localization of the first bone tunnel produced is known and will be able to serve for the surgeon to locate themselves in their working space in order to produce a second bone tunnel without the latter interfering with the first bone tunnel.

In one embodiment, the real-time assistance system is further adapted to display, on the first projection, the first pattern (i.e. the first two-dimensional view of said three-dimensional representation of the first bone tunnel) and, on the second projection, the second pattern (i.e. the second two-dimensional view of said three-dimensional representation of the first bone tunnel).

In one embodiment, the real-time assistance system is further adapted to calculate a three-dimensional representation of the first bone tunnel produced.

The display of the three-dimensional representation calculated thus makes it possible to check for example whether the first bone tunnel produced is indeed produced in the bone over its entire length and whether it has sufficiently thick walls not to risk fracturing the first bone tunnel during the implementation of means for fixing an intra-tunnel graft (such as interference screws). Fracturing a tunnel is known by the English term 'cortical wall blow out'. Thus, if the surgeon knows that they have shaved the cortical, they can as a precaution choose to use an extra-tunnel fastening mean, such as a button.

In one embodiment, the real-time assistance system is further adapted to calculate an intersection between the current estimation of the localization zone of the first, respectively of the second, orifice and, on one hand the first pattern (i.e. the first two-dimensional view), on another hand the second pattern (i.e. the second two-dimensional view).

This allows, after a production of a first bone tunnel in the joint of the patient, if the surgeon must produce a second bone tunnel, to know the position thereof in real time with respect to the position of the first bone tunnel already produced.

In one embodiment, the real-time assistance system is further adapted when the intersection with the first (i.e. the first two-dimensional view), respectively second pattern (i.e. the second two-dimensional view), comprises at least one portion of the first pattern (i.e. the first two-dimensional view), respectively a portion of the second pattern (i.e. the second two-dimensional view), to display an information message on the first, respectively second, superimposition.

The display of an information message assists the surgeon in real time to adjust the current position and orientation of their surgical piercing instrument.

Another aspect of the invention relates to a computer-implemented method for assisting the production of at least one bone tunnel by arthroscopy in a joint of a patient using a surgical piercing instrument, said method comprising:

obtaining a preoperative three-dimensional anatomical model specific to the patient, said model comprising a representation of at least one portion of interest of the joint of the patient and a representation of anatomical structures of interest, acquiring monitoring information of the current position and orientation of the surgical piercing instrument during a manipulation of said surgical piercing instrument by an operator using the monitoring device;

determining a peroperative partial three-dimensional anatomical model, comprising a representation of said at least one portion of interest of the joint, by:

acquiring, using an imaging device, a stream of peroperative two-dimensional images of portions of interest of the joint of the patient, said peroperative two-dimensional images comprising said at least one portion of interest of the joint, and acquiring monitoring information of the current position and orientation of said imaging device using a monitoring device; wherein said peroperative partial three-dimensional anatomical model is obtained from the stream of peroperative bidimensional images and said monitoring information of the current position and orientation, or acquiring, using a measuring device, a cloud of points representative of said at least one portion of interest of the joint, and acquiring monitoring information of the current position and orientation of said measuring device; wherein said peroperative partial three-dimensional anatomical model is obtained from said cloud of points;

registering the preoperative three-dimensional anatomical model on the peroperative partial three-dimensional anatomical model;

calculating, on the basis of information obtained with the registering of the preoperative three-dimensional anatomical model, and of the current position and orientation of the surgical piercing instrument:

a current zone of localization, in a current peroperative two-dimensional image, of a piercing end of the surgical piercing instrument, a first projection comprising a current estimation of a zone of localization of a first orifice of a bone tunnel to be produced, a second projection comprising a current estimation of a zone of localization of a second orifice of a bone tunnel to be produced.

Another aspect of the invention relates to a computer program product comprising instructions that lead the system described above to implement the steps of the method according to the present invention.

In one embodiment, the invention relates to a computer program product comprising instructions for implementing the following steps of a method for real-time assistance in the production of at least one bone tunnel by arthroscopy in a joint of a patient during the execution of the program by a processor of a programmable device:

obtaining a preoperative three-dimensional anatomical model specific to the patient, said model comprising a representation of the joint of the patient and a representation of anatomical structures of interest, acquiring, using an imaging device, a stream of peroperative two-dimensional images, said peroperative two-dimensional images comprising a portion of interest of the joint, acquiring monitoring information of the position and orientation of a surgical piercing instrument during a manipulation of the surgical piercing instrument by an operator using a monitoring device, determining a peroperative partial three-dimensional anatomical model from the stream of peroperative two-dimensional images and/or from a cloud of points representative of the portion of interest of the joint obtained using a measuring device, registering the preoperative three-dimensional anatomical model on the peroperative partial three-dimensional anatomical model;

calculating, on the basis of information obtained with the registering of the preoperative three-dimensional anatomical model and of the current position and orientation of the surgical piercing instrument: a current zone of localization, in a current peroperative two-dimensional image of a piercing end of the surgical piercing instrument, a first projection comprising a current estimation of a zone of localization of a first orifice of a bone tunnel to be produced, a second projection comprising a current estimation of a zone of localization of a second orifice of a bone tunnel to be produced.

In one embodiment, the invention relates to a method for real-time assistance in the production of at least one bone tunnel by arthroscopy in a joint of a patient, comprising the following steps:

obtaining a preoperative three-dimensional anatomical model specific to the patient, said model comprising a representation of the joint of the patient and a representation of anatomical structures of interest,

acquiring, using an imaging device, a stream of peroperative two-dimensional images, said peroperative two-dimensional images comprising a portion of interest of the joint, acquiring, using a monitoring device, monitoring information of the position and orientation of a surgical piercing instrument during a manipulation of said surgical piercing instrument by an operator, determining a peroperative partial three-dimensional anatomical model from the stream of peroperative two-dimensional images and/or from a cloud of points representative of the portion of interest of the joint obtained using a measuring device, registering the preoperative three-dimensional anatomical model on the peroperative partial three-dimensional anatomical model;

calculating, on the basis of information obtained with the registering of the preoperative three-dimensional anatomical model, and of the current position and orientation of the surgical piercing instrument:

a current zone of localization, in the two-dimensional image, of a piercing end of the surgical piercing instrument, a first projection comprising a current estimation of a zone of localization of a first orifice of a bone tunnel to be produced, a second projection comprising a current estimation of a zone of localization of a second orifice of a bone tunnel to be produced.

Another aspect of the invention relates to a computer-readable support (non-transitory) on which the computer program described above is recorded.

The present invention relates to a system for real-time assistance 1 in the production of at least one bone tunnel by arthroscopy in a joint of a patient. In the present description, the joint is one of the knees of the patient. By bone tunnel, it is meant a tunnel produced in a bone of the patient, notably the femur or the tibia, and intended to receive a neoligament.

Installation of a neoligament of the knee implies piercing the femoral and/or tibial ends for the neoligament passage, these piercings constituting the aforementioned bone tunnel.

BRIEF DESCRIPTION OF THE FIGURES

The sub-figures of FIG. 8 are various examples of two-dimensional projections of parts of the knee and according to various directions.

DETAILED DESCRIPTION

Figure 1:
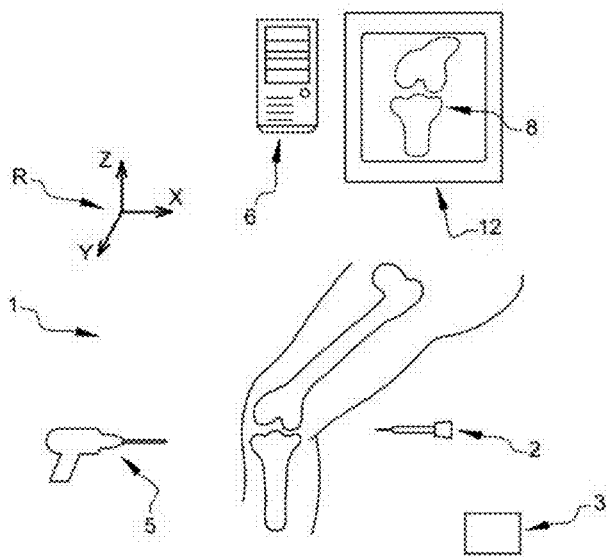
FIG. 1 is a representation of a system for real-time assistance in the production of a bone tunnel according to one or several embodiments of the invention.

The real-time assistance system 1, represented in FIG. 1, comprises an imaging device 2 able to acquire two-dimensional images of portions of the joint of the patient, a monitoring device 3 and a programmable device 6.

The imaging device 2 is for example an arthroscope. An arthroscope is a thin tube equipped with a miniaturised lens connected to a camera allowing to visualize the interior of a joint. The arthroscope is inserted into the joint after incision thereof. The diameter of the arthroscope is of the order of a few millimetres. During an operation by arthroscopy on the joint of the patient, the imaging device 2 acquires a stream, preferably continuous, of two-dimensional images of all or part of the joint of the patient.

Furthermore, during an operation by arthroscopy to produce one or more bone tunnels, a surgeon uses a surgical piercing instrument 5 such as a surgical motor, comprising a piercing end. The piercing end allows to produce tunnels in the bone structures. For example, the end of the surgical piercing instrument 5 is a drill or a broach. The monitoring device 3 comprises for example one or more cameras allowing to locate and track in real time the position in space of the various instruments used during the operation, such as the imaging device 2 and the surgical piercing instrument 5. On the imaging device 2 and the surgical piercing instrument 5 are fixed one or more markers configured to emit, receive or reflect an electromagnetic radiation, so as to be located by the monitoring device 3. Advantageously, one or more passive markers can be fixed on to the imaging device 2 and the surgical piercing instrument 5, so as to be visible on images acquired by the monitoring device 3. For example, the passive markers are QR codes, AR tags or 3D markers. Furthermore, the system 1 is configured to receive measurements obtained using a measuring device, for example a contact sensor. This measuring device allows to obtain a cloud of points representative of the contact surface, in the case of the present invention of the surface of the portion of interest of the joint. The measuring device can be mounted on a robotic arm or be coupled with a marker rigidly secured on the sensor itself. If a marker is used, the latter can be located in space by the monitoring device 3 or another equivalent monitoring device. Alternatively, the measuring device can be a depth camera (for example: 'ToF or Time of Flight' camera, 'LiDAR', a Kinect camera, an RGB-D camera, etc.) configured to acquire images, in grey levels or colour, which indicate the distance between the camera and the objects of the scene. These images allow to obtain a cloud of 3D points representative of objects of the scene. In an alternative embodiment, the system 1 may further comprise said measuring device.

The position in space of the imaging device 2 and of the piercing instrument 5 with respect to the monitoring device 3 can then be known by triangulation.

Advantageously, if the geometry of each monitored instrument such as the imaging device 2 and the piercing instrument 5 is known, the monitoring device 3 directly recognises these without equipping them with markers and their respective position and orientation with respect to the monitoring device is known.

For example, the monitoring device 3 is a system of the Hololens™ type allowing to locate, using cameras, among others, the imaging device 2 and the surgical piercing instrument 5 in an operating theatre. Thus, as soon as the imaging device 2 or the surgical piercing instrument 5 are in the field of vision of the cameras, this or these are located and their positions are calculated and recorded.

The programmable device 6 is a processing device that can for example be a computer, a microprocessor, an integrated circuit, or a programmable logic device (PLD). The programmable device 6 can also comprise one or more graphics processors (GPUs).

The programmable device 6 is configured to execute instructions stored on a computer-readable support, such as an integrated circuit, a hard disk, a CD, a DVD, a RAM memory or a ROM memory.

According to an embodiment, the real-time assistance system 1 is adapted to help with the production of one or more bone tunnels during an operation by arthroscopy in a knee of a patient requiring a graft of one or more ligaments.

Figure 2:
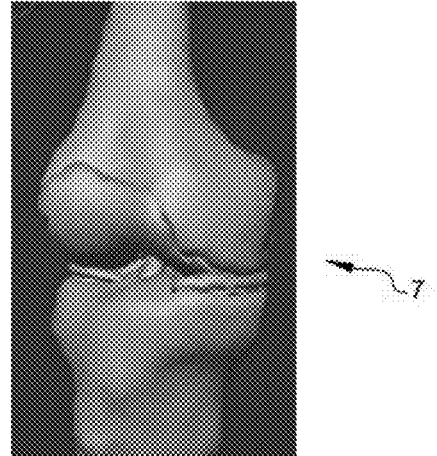
FIG. 2 represents an example of a preoperative three-dimensional model of a portion of interest of a joint of a patient.

Prior to the operation, during a preoperative phase, a preoperative three-dimensional model 7 of a portion of interest of the knee 8 is obtained as described below. Such a preoperative three-dimensional model 7 is for example shown on FIG. 2. The portion of interest of the knee 8 comprises the zones of the knee where the graft of the ligament or ligaments must be implemented.

Data are obtained in advance by magnetic resonance imaging (MRI). The data comprise various slices of the portion of interest of the knee 8. By 'slice', it is meant a two-dimensional image. The various slices are slices in planes parallel respectively to the sagittal, axial and coronal planes as defined in the magnetic resonance imaging field. The MRI technique can be two-dimensional, i.e. based on sequential acquisition triplets, or three-dimensional, i.e. based on volumetric acquisitions. Alternatively, other techniques allowing to acquire several slices of zones of interest can be used, such as for example computational axial tomography.

A preoperative programmable device generates, by applying a reconstruction algorithm to the data, the preoperative three-dimensional model 7.

The magnetic resonance imaging technique presents the advantage of providing data relating to anatomical structures that are not accessible by techniques such as radiography. Thus, the three-dimensional model 7 can comprise, for example, apart from a representation of the bone contours of the femur, of the tibia, of the patella and of the head of the fibula, a representation of the cartilaginous contours of the femur, of the tibia, a complete or partial representation of the anterior cruciate ligament, of the posterior cruciate ligament, of the external lateral ligament, of the internal lateral ligament, of the femoropatellar ligament.

Figure 3:
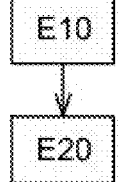
FIG. 3 represents a flowchart of the steps implemented during an reconstruction algorithm of three-dimensional model according to one or several embodiments.

Advantageously, the reconstruction algorithm comprises two successive steps E10 and E20. FIG. 3 represents a flowchart of the various steps of the reconstruction algorithm.

In a first step E10, the data acquired by MRI, for a plurality of subjects, are segmented and labelled, so as to generate a training database. A deep neural network of the CNN ('Convolutional Neural Network') type can be trained on said training database so as to generate as output a segmentation of the anatomical structures when the network receives as input at least one 3D image or a collection of 2D slices, representing the portion of interest of the knee 8 of the patient (i.e. data acquired by MRI). According to a first option, a convolutional artificial neural network of the RCNN ('Region-based Convolutional Neural Network') type, such as the YOLACT++ architecture, can for example be used. The operation of such a network is for example described in the article 'YOLACT++ Better Real-Time Instance Segmentation'. The model implemented by this type of artificial networks, once trained, makes the prediction, in other words, the detection, the segmentation and the classification of structures present in each slice. Following the predictions, the slices are merged first of all by cutting plane (axial, sagittal or coronal) using a 'slice matching' algorithm to generate three first 3D models. Then, an inter-plane merging of these three first 3D models is done using a 3D/3D registration. The preliminary 3D model generated is then obtained by refinement with a filtering algorithm and by elimination of outlier data.

Other types of artificial neural networks can be used, such as the RCNN (Fast, Faster, Mask RCNN), Computer Vision, U-net, MeshCNN and SDU-Net networks. According to a second option, a neural network of the 3D CNN+ type (i.e.

a type of convolutional neural network used for analysing three-dimensional data) can be used.

Once option 1 or 2 has been implemented, a preliminary three-dimensional model can then be reconstituted, for example by using techniques described in the patents FR2920565B1 or U.S. Pat. No. 7,123,255.

The preliminary three-dimensional model may include errors (for example, badly reconstructed anatomical structures) or present incomplete elements (after-effects for example of the trauma that the patient suffered).

The second step E20 of the reconstruction algorithm aims to correct the preliminary three-dimensional model, on the basis of teachings derived from the literature in relation to the anatomy of the knee, as will be explained below.

A first type of correction made during the second step is the repositioning of a structure wrongly placed during the generation of the preliminary three-dimensional model.

Figure 4:
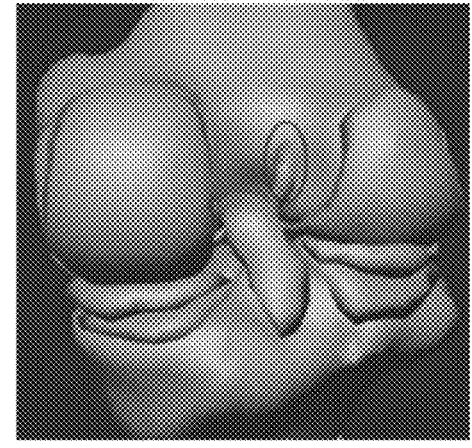
FIG. 4 represents a first type of correction made during step E20 of the flowchart of FIG. 3.
Figure 4:
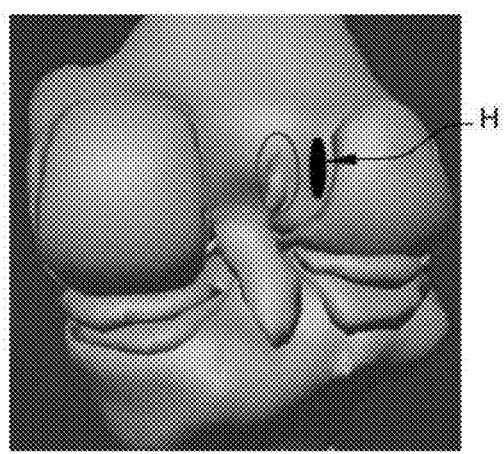

FIG. 4, on the left, shows encircled the femoral insertion structure of the anterior cruciate ligament. On this FIG. 4, this femoral insertion structure is wrongly positioned. Thus, in the second step E20, this femoral insertion structure is repositioned at the correct localization, denoted H, as indicated on FIG. 4, on the right.

The correct localization is for example known from the literature relating to the anatomy of the knee. Thus, the repositioning from the incorrect position to the correct position is for example done manually by a designer in the light of this knowledge. In another example, from geometric models described in the literature mentioned above (such as a quantified distance, a quantified radius of curvature), a curve or surface reconstruction algorithm will be applied to the wrongly positioned element. In yet another example, the repositioning is done using a neural network trained on a database of 3D models obtained from step E10. By way of illustration, a network such as the 3D CNN network can be used.

A second type of correction made during the second step is the completion of incomplete elements.

Figure 5:
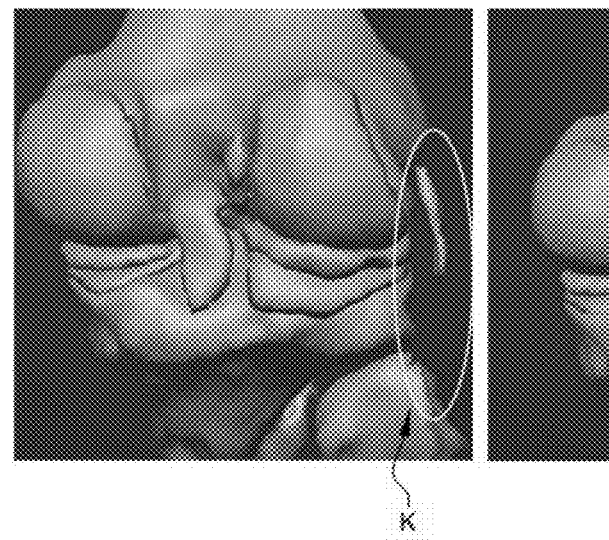
FIG. 5 represents a second type of correction made during step E20 of the flowchart of FIG. 3.
Figure 5:
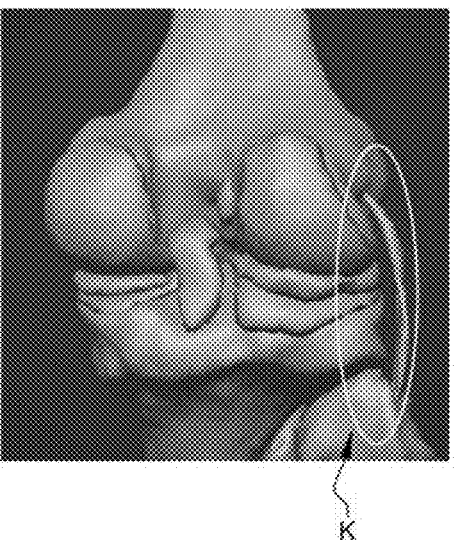

FIG. 5, on the left, illustrates, inside the oval form K a representation of the external lateral ligament in the preliminary three-dimensional model. This representation is incomplete. Thus, in the second step, this representation will be completed as illustrated on FIG. 5, on the right.

Methods similar to those used for implementing the first type of correction can be used for implementing this second type of correction.

It will now be described how the real-time assistance system 1 operates in peroperative phase, i.e., during the operation by arthroscopy by a surgeon in the knee of the patient requiring a graft of one or several ligaments.

During the operation, the surgeon manipulates a surgical piercing instrument 5 of the surgical motor type provided with a drill or a broach. The surgical piercing instrument 5 is used for initially marking skin zones to make incisions at the appropriate locations in the knee of the patient in order to produce the bone tunnel or tunnels.

One aspect of the invention relates to the ability of the real-time assistance system 1 to allow to visualize in real time, and before implementing the surgical act, when the surgeon manipulates the surgical piercing instrument 5 in order to produce a bone tunnel 10, a first orifice 11a representing the entrance of the bone tunnel and a second orifice 11b representing the exit of the bone tunnel. The first orifice 11a and the second orifice 11b are determined, as will be described hereinafter, according to the position and the orientation, in real time, of the end of the surgical piercing instrument 5. By 'entrance' of the bone tunnel 10, it is meant the surface zone of the bone structure through which the end of the surgical piercing instrument 5 enters. By 'exit' of the bone tunnel, it is meant the surface zone of the bone structure through which the end of the surgical piercing instrument 5 exits. Ultimately, the system allows to see in real time the position that the entry and exit orifices (respectively orifices 11a and 11b) would occupy if the surgeon were to continue the piercing operation with the piercing instrument according to the trajectory defined by the position and the orientation of the instrument.

Thus, through the real-time visualization of the localization of the first orifice 11a and of the second orifice 11b, the surgeon will be able to adjust the position and the orientation in space, with respect to the knee, of the surgical piercing instrument 5, to correctly position the bone tunnel 10 with respect to anatomical structures of interest that are known anatomical references, and without damaging 'noble' anatomical structures, such as adjacent tendinous or ligamentous structures.

Prior to the operation, the programmable device 6 received the preoperative three-dimensional model 7 generated by the preoperative programmable device. The preoperative three-dimensional model 7 is for example stored in a memory associated with the programmable device 6 or in a database accessible to the programmable device 6.

The position of the knee of the patient with respect to the surgical piercing instrument 5 and to the imaging device 2 must be known at every moment.

To do this, for example, markers, such as pins, can be positioned in the femur or the tibia to create a referential R. The referential R serves to know the position of the knee to be operated with respect to the surgical piercing instrument 5. The monitoring device 3 allows to capture the information on the position and orientation of the markers fixed to the patient. The referential R allows to implement the registration of the preoperative three-dimensional model 7 on the knee of the patient. Thus, the real-time position of the knee of the patient in the space of the operating theatre is known.

Alternatively, given that the imaging device 2 acquires a stream of images, the position of the knee in the space of the operating theatre can be known from the stream of images. Indeed, it is possible to obtain, from the stream of images a current partial three-dimensional model and to register the preoperative three-dimensional model 7 on the current partial three-dimensional model. In particular, the distance between the imaging device 2 and the anatomical structures for which the latter produces the image, may be known. Thus, the position of the knee in the space, can be known after registration.

The programmable device 6 of the real-time assistance system 1 can be configured to drive the ensemble of equipment used during the operation. Thus, the programmable device 6 is configured to receive signals from the monitoring device 3, and to calculate, on the basis of these signals, the real-time position and orientation in the space of the operating theatre of the elements of interest tracked by the monitoring device 3 (i.e. the femur and the tibia of the patient, the imaging device 2, the surgical piercing instrument 5 and optionally the measuring device).

A peroperative partial three-dimensional model 9 of the portion of interest of the knee 8 is generated by the programmable device 6. The term 'partial' refers to the fact that the model relates solely to all or part of the portion of interest of the knee and not to the whole of the anatomical structure of the knee. It is reminded that the portion of interest of the knee 8 comprises the zones of the knee where the graft of the ligament or ligaments must be implemented.

Various methods can be used for generating the peroperative partial three-dimensional model 9.

In an embodiment, an operator (who may be the surgeon or any other qualified person assisting to the operation) probes using a sensor (i.e. the measuring device), on which a marker is fixed, points on the surface of the knee of the patient. The marker can be located. The marker fixed to the sensor allows to know the position in space of each point of the cloud of points obtained. Alternatively, a sensor mounted on a robotic arm can be used. In an alternative embodiment, a depth camera (i.e. the measuring device) can be used to acquire a cloud of points representative of the surface of the portion of interest of the knee 8. In all cases, the measuring device allows to acquire the cloud of points representaive of the portion of interest of the joint, notably representaive of the surface of the portion of interest of the joint. An algorithm then generates at least one three-dimensional surface from this cloud of points, corresponding for example to a part of the femoral condyle in three dimensions. A 'bone morphing' algorithm can for example be used. This or these algorithm(s) can be executed by the programmable device 6 in order to generate the peroperative partial three-dimensional model 9. Alternatively, an auxiliary programmable device can execute the algorithm(s) and send the peroperative partial three-dimensional model 9 generated to the programmable device 6.

In another example, the two-dimensional images acquired by the imaging device 2 can be used to generate the peroperative partial three-dimensional model 9 in real time using depth maps generated from the stream of images recorded by the imaging device 2 and from a SLAM ('simultaneous localization and mapping') algorithm executed by the programmable device 6. Here, the stream of images is monocular. Thanks to the monitoring device 3, the position in space of the imaging device 2 that generates the video stream from which the partial three-dimensional model is generated is known in real time, and thus the three-dimensional position of the peroperative partial three-dimensional model 9 in space and also the position in space of the preoperative three-dimensional model 7 are known in real time.

Advantageously, an algorithm of the SLAM type is used to calculate the current partial three-dimensional model 8. Algorithms of the SLAM type allow, from the use of two-dimensional images acquired by an image sensor, and from the position in space of the image sensor, to produce, by means of predictions of depth maps associated with the two-dimensional images, a three-dimensional mapping of the scene observed in the two-dimensional images. The three-dimensional mapping obtained can then be located in a referential associated with the image sensor that acquires the two-dimensional images. Moreover, this three-dimensional mapping is dynamic. In other words, it can be obtained in real time, as the image sensor acquires the two-dimensional images of the scene. A description of the algorithms of the SLAM type can be found in the article "*Visual SLAM algorithms: a survey from* 2010 *to* 2016", T. Taketomi et al., IPSJ Transactions on Computer Vision and Applications (2017).

Figure 6:
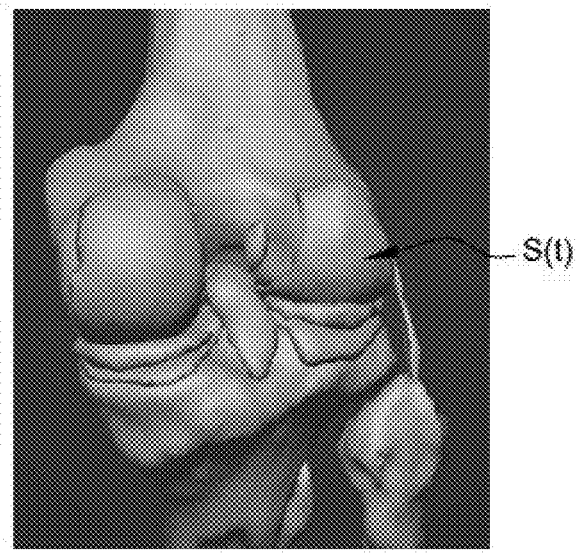
FIG. 6 represents a superimposition of a peroperative partial three-dimensional model and of a preoperative three-dimensional model according to one or several embodiments of the invention.

Once the peroperative partial three-dimensional model 9 has been generated, the programmable device 6 executes, in real time, a 3D/3D registration algorithm for superimposing in real time the preoperative three-dimensional model 7 on the peroperative partial three-dimensional model 9. A 3D/3D registration advantageously allows to obtain a more precise superimposition than in the case of a 2D/3D registration. Such a superimposition is represented on FIG. 6. For example, an algorithm minimizing the distance between corresponding points can be used. Thus, a superimposition S(t) can be displayed on a visualization screen visible to the surgeon, so that the latter can in real time view, on the basis of the match between the preoperative three-dimensional model 7 and the peroperative partial three-dimensional model 9 the position of the anatomical structures represented in the preoperative three-dimensional model with respect to the real position of the structures represented in the peroperative partial three-dimensional model 9. Indeed, a precise registration allows to locate with precision the piercing tool and thus to better calculate the information allowing to anticipate the position of the bone tunnel, thus reducing the risks of error for the surgeon.

For example, the superimposition S(t) can be used for locating the cutaneous incision zones on the skin.

In addition, once the peroperative partial three-dimensional model 9 has been superimposed on the preoperative three-dimensional model 7, three parts of the knee of the patient can be defined on the superimposition S(t), for example, by implementing a division algorithm by the programmable device 6.

Figure 7:
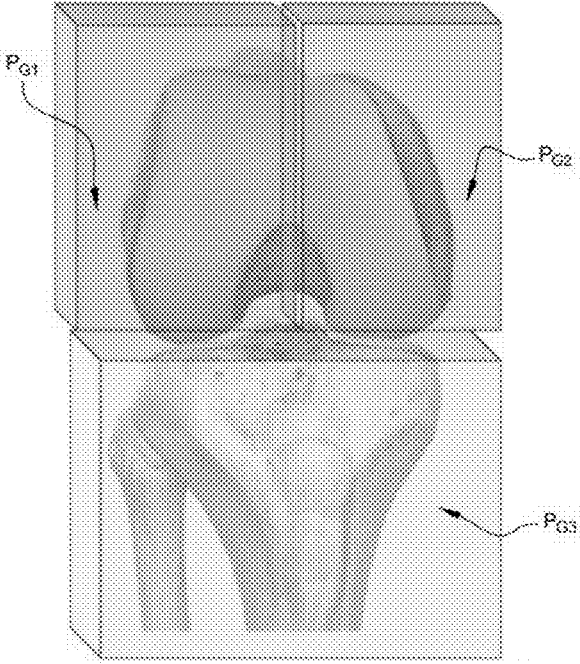
FIG. 7 represents a partitioning of a knee according to one or several embodiments of the invention.

For example, the division algorithm creates in real time three volumes on the peroperative partial three-dimensional model 9 by: separating the femur and the tibia by a plane passing through the articular interline; separating the femur into two compartments (internal and external) at a sagittal plane perpendicular to the plane of the joint interline and passing through the apex of the notch. As shown on FIG. 7, a first part $P_{G1}$ corresponds to the volume occupied by the external condyle; a second part $P_{G2}$ corresponds to the volume occupied by the internal condyle; finally, a third part $P_{G3}$ corresponds to the volume occupied by the tibial epiphysis of the patient.

Moreover, prior to the operation of producing the bone tunnels by the surgeon, the programmable device 6 executes an algorithm of calculation and generation of a plurality of two-dimensional projections of the preoperative three-dimensional model 7. This generation of two-dimensional images allows to represent or display the preoperative three-dimensional model, which is a 3D object, on a two-dimensional medium such as a computer screen. By projection, it is meant a view of the preoperative three-dimensional model 7. A projection in geometric perspective or an orthogonal (or parallel) projection can be calculated and generated.

For example, the calculation algorithm separates, first of all, the femur from the tibia according to a plane passing through the articular interline. The femoral epiphysis is obtained from which the first part $P_{G1}$ and the second part $P_{G2}$ are determined after a division of this femoral epiphysis according to a sagittal plane passing through the centre of the roof of the notch. Moreover, the tibial epiphysis is obtained from which the third part $P_{G3}$ is determined. These three parts (i.e. the three volumes on the peroperative partial three-dimensional model 9) $P_{G1}$, $P_{G2}$ and $P_{G3}$ are then used to generate said plurality of two-dimensional projections.

These two-dimensional projections are stored in the memory associated with the programmable device 6 and will be dedicated, as will be described hereinafter, to an automatic display determined according to the current position at an instant t of the various elements of the real-time assistance system.

Figure 8:
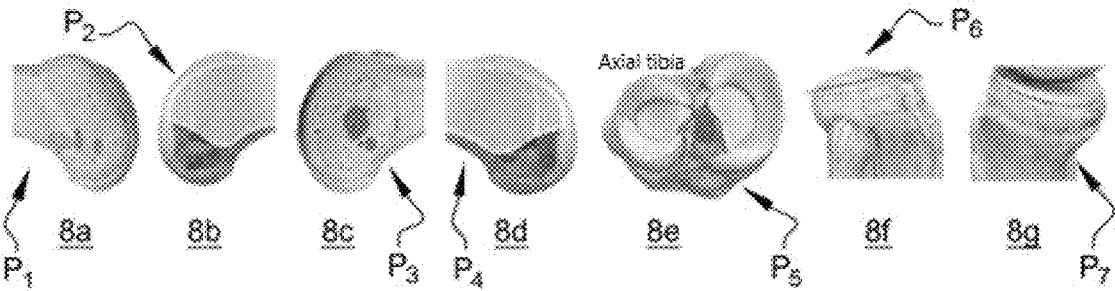
FIG. 8*h* and FIG. 8*i* are schematic representations of a femoral epiphysis and of a tibial epiphysis.
Figure 8H:
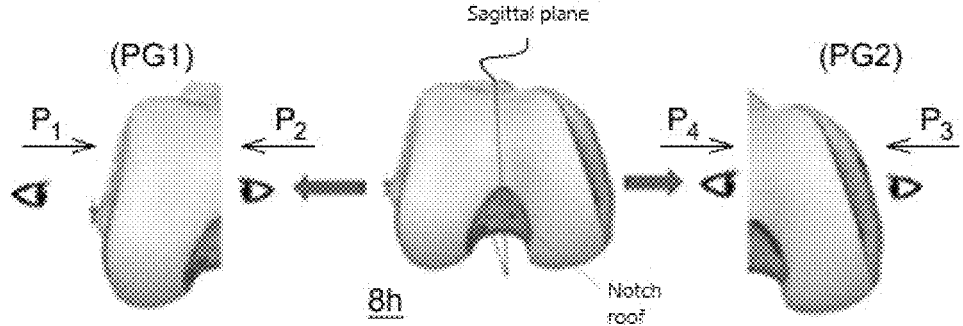
Figure 8I:
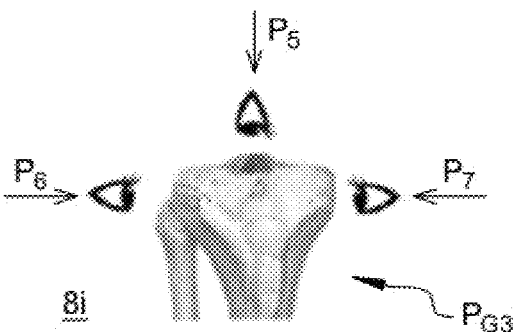

With reference to FIGS. 8a to 8g, these projections are respectively:

an external projection (or lateral view) of the external condyle $P_1$, illustrated on FIGS. 8a and 8h, an internal projection (or medial view) of the external condyle $P_2$, illustrated on FIGS. 8b and 8h (i.e. image of the slice along a sagittal plane passing through the centre of the roof of the notch), an external projection (or medial view) of the internal condyle $P_3$, illustrated on FIGS. 8c and 8h, an internal projection (or lateral view) of the internal condyle $P_4$, illustrated on FIGS. 8d and 8h (i.e. image of the slice along the sagittal plane passing through the centre of the roof of the notch), an axial projection (or view) of the tibia $P_5$, from the illustrated on FIGS. 8e and 8i, an external projection of the tibia, or lateral view of the tibia $P_6$, illustrated on FIGS. 8f and 8i, an internal projection of the tibia, or medial view of the tibia $P_7$, illustrated on FIGS. 8g and 8i.

These various projections comprise the corresponding projections of the anatomical structures of interest.

Figure 9:
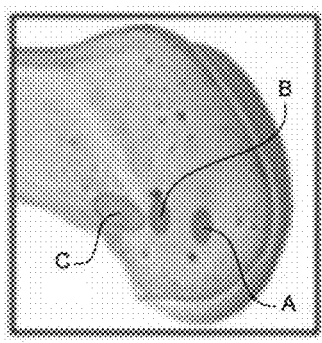
FIG. 9 represents a two-dimensional projection of a portion of interest of a knee of a patient with several projections of anatomical structures of interest according to one or several embodiments.

FIG. 9 is an example of the external projection (or lateral view) of the external condyle $P_1$. It may be observed thereon: the femoral insertion zone A of the popliteal tendon, the femoral insertion zone B of the external lateral ligament, and the insertion zone of the anterolateral ligament C. These various elements represent the projections of the corresponding structures in the preoperative three-dimensional model 7 resulting from step E20.

Figure 10:
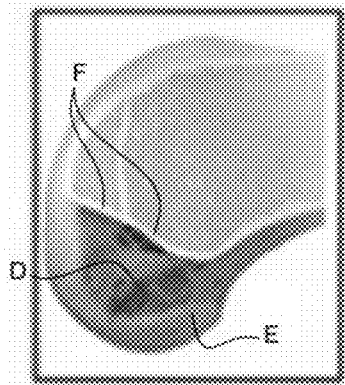
FIG. 10 represents another two-dimensional projection of a portion of interest of a knee of a patient with several projections of anatomical structures of interest according to one or several embodiments.

FIG. 10 is an example of the internal projection (or medial view) of the external condyle $P_2$. It may be observed thereon: the insertion surface D of the anterior cruciate ligament, the inferior cartilaginous boundary E, the proximal boundary of the inter-condyle notch and the roof of the notch.

Typically, on FIG. 9, the insertion zone of the anterolateral ligament was not identifiable in the preliminary three-dimensional model obtained during the preoperative phase of acquisition of the data by magnetic resonance imaging and generation of the three-dimensional model 7. This zone was typically reconstructed during the second step (E20) of the reconstruction algorithm aiming to correct the preliminary three-dimensional model.

During the operation, the imaging device 2 of the real-time assistance system 1 captures in real time a continuous stream of two-dimensional images. At each instant t, the surgeon can view on a visualization device 12 such as a screen a current two-dimensional image I(t) of the portion of interest of the knee 8.

Moreover, still during the operation, the programmable device 6 receives in real time a signal coming from the monitoring device 3, on the basis of which it calculates the position and the orientation $D_I(t)$ in real time of the imaging device 2 with respect to the referential R. The position and the orientation $D_I(t)$ comprise for example three coordinates and three angles.

Also, still during the operation, the programmable device 6 receives in real time a signal coming from the monitoring device 3, on the basis of which it calculates the position and the orientation $I_P(t)$ in real time of the piercing end of the surgical piercing instrument 5. The position and the orientation $I_P(t)$ comprise for example three coordinates and three angles.

Figure 11:
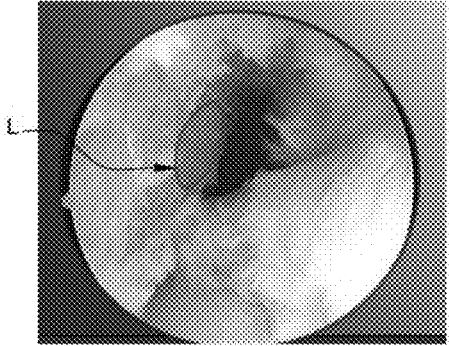
FIG. 11 represents a superimposition of a peroperative two-dimensional image with a current localization zone of an end of a surgical piercing instrument according to one or several embodiments.

Thus, with the real-time assistance system 1, it is possible to superimpose a current localization zone L of the piercing end of the surgical piercing instrument 5 on the current two-dimensional image I(t). Such a superimposition is represented on FIG. 11.

It will now be described how, in another aspect of the invention, the real-time assistance systems 1 allows the surgeon to position and orient the surgical piercing instrument 5 adequately, before making the piercing of the bone tunnel, in order not to damage anatomical structures to be preserved during the piercing.

A first projection $P_a$ and a second projection $P_b$ among the projections $P_1$ to $P_7$ will be displayed on a first auxiliary visualization screen and a second auxiliary visualization screen, according to the current position and orientation of the end of the surgical piercing instrument 5 and/or of the imaging device 2. By 'current', it is meant actual, i.e. corresponding to the actual instant t of the operation.

At the actual instant t of the operation, the current position and orientation of the end of the surgical piercing instrument 5 and/or of the imaging device 2 are known by thanks to the second monitoring device 3 and are collected and recorded by the programmable device 6.

According to the position and/or the orientation in one from the first part $P_{G1}$, the second part $P_{G2}$ and the third part $P_{G3}$, the selection of the projections $P_a$ and $P_b$ is made in accordance with the following rules.

If the end of the surgical piercing instrument 5 is in (or in proximity to) the first part $P_{G1}$ (volume occupied by the external condyle), the first projection $P_a$ is the external projection (or lateral view) of the external condyle $P_1$, and the second projection $P_b$ is the internal projection (or medial view) of the external condyle $P_2$.

The real-time position of the first part $P_{G1}$, of the second part $P_{G2}$, and of the third part $P_{G3}$ is determined by means of the real-time knowledge of the position of the knee of the patient in the space of the operating theatre. Indeed, the first part $P_{G1}$, the second part $P_{G2}$, and the third part $P_{G3}$ are calculated by the division algorithm previously described, applied to the preoperative three-dimensional model 7. The latter is registered in real time on the peroperative partial three-dimensional model 9, the position of which in the space of the operating theatre is known using the real-time position of the knee of the patient.

If the end of the surgical piercing instrument 5 is in (or in proximity to) the second part $P_{G2}$ (volume occupied by the internal condyle), the first projection $P_a$ is the external projection (or medial view) of the internal condyle $P_1$, and the second projection $P_b$ is the internal projection (or lateral view) of the internal condyle $P_2$.

If the end of the surgical piercing instrument 5 is in (or in proximity to) the third part $P_{G3}$ (volume occupied by the tibial epiphysis) and is oriented downwardly, the first projection $P_a$ is the external projection of the tibia (or lateral view of the tibia) $P_6$, and the second projection $P_b$ is the internal projection of the tibia (or medial view of the tibia) $P_7$.

If the end of the surgical piercing instrument 5 is in (or in proximity to) the third part $P_{G3}$ (volume occupied by the tibial epiphysis) and is oriented upwardly, i.e. so as to intersect the plane of the articular interline), the first projection $P_a$ is displayed and corresponds to the axial projection of the tibia $P_5$, and the second projection $P_b$ corresponding to the internal projection of the tibia (or medial view of the tibia) $P_7$.

These rules were determined in order to facilitate and make more intuitive the manipulation of the piercing instrument 5 by ensuring consistency of the selection of the first projection $P_a$ and of the second projection $P_b$ with the current position and orientation of the surgical piercing instrument 5. Other rules for facilitating and making more intuitive the manipulation of the piercing instrument 5 can be determined by a person skilled in the art.

Advantageously, when the surgeon positions and orients the end of the surgical piercing instrument 5 in order to produce a bone tunnel 10, the programmable device 6 executes an algorithm for calculating a current estimation of the current localization zone L, in the current peroperative two-dimensional image I(t), of the piercing end of the surgical piercing instrument 5. Furthermore, the programmable device 6 executes an algorithm for calculating a current estimation of a localization zone of a first orifice 11a of the bone tunnel 10 to be produced, in the first projection $P_a$, and a current estimation of a localization zone of a second orifice 11b of the bone tunnel 10 to be produced, in the second projection $P_b$, for said current position and orientation $I_P(t)$ of the end of the surgical piercing instrument 5. The calculations are done on the basis of information obtained with the registration of the preoperative three-dimensional anatomical model with the peroperative partial three-dimensional anatomical model (on the basis of the knowledge of the real-time position in the space of the operating theatre of the preoperative three-dimensional model—resulting from step E20—registered in real time on the peroperative three-dimensional model 9) and of the current position and orientation $I_P(t)$ of the surgical piercing instrument 5. Advantageously, the localization zone of the first orifice 11a of the bone tunnel 10 to be produced is superimposed on the first projection $P_a$. Likewise, advantageously, the localization zone of the second orifice 11b of the bone tunnel 10 to be produced is superimposed on the second projection $P_b$. Notably, the programmable device 6 is configured to produce a superimposition image to be displayed on the visualization unit comprising this superimposition the localization zone of the first orifice 11a of the bone tunnel 10 on the first projection $P_a$. Likewise, the programmable device 6 is configured to produce a superimposition image to be displayed on the visualization unit comprising this superimposition the localization zone of the second orifice 11b of the bone tunnel 10 on the second projection $P_b$.

The first orifice 11a corresponds for example to the entry orifice of the bone tunnel 10 and the second orifice 11a then corresponds to the exit orifice of the bone tunnel 10, or vice versa.

Figure 12A:
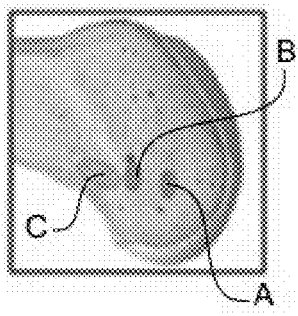
FIG. 12*a* represents a superimposition of a first orifice of a bone tunnel to be produced on a first two-dimensional projection according to one or several embodiments.

FIG. 12a represents the external projection of the external condyle $P_1$ of FIG. 8a, where a circle representaive of the localization zone of the first orifice 11a of the bone tunnel 10 has been superimposed. On FIG. 12a, the circle intersects with the femoral insertion zone of the popliteal tendon B. Such a position of the first orifice 11a of the bone tunnel 10 cannot thus be envisaged since it would damage the femoral insertion zone of the popliteal tendon B.

Figure 12B:
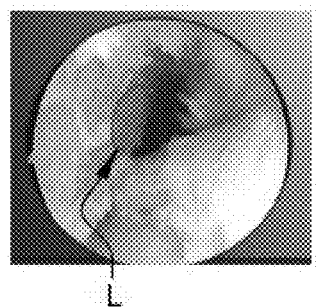
FIG. 12*b* is another example of superimposition of a peroperative two-dimensional image with a current localization zone of an end of a surgical piercing instrument according to one or several embodiments such as the superimposition of FIG. 11.
Figure 12C:
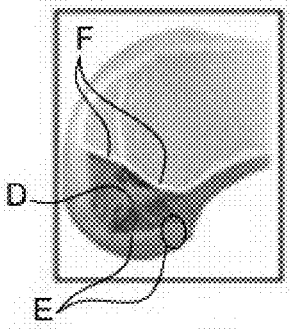
FIG. 12*c* represents a superimposition of a second orifice of the bone tunnel to be produced in FIG. 12*a* on a second two-dimensional projection according to one or several embodiments.

FIG. 12c represents the interior projection of the external condyle $P_2$ (i.e. slice) of FIG. 8b, where a circle representative of the localization zone of the second orifice 11b of the bone tunnel 10 has been superimposed. On FIG. 12c, the circle intersects with the insertion zone of the anterolateral ligament E. Such a position of the second orifice 11b of the bone tunnel 10 is therefore not conceivable since the latter would damage the femoral insertion zone of the anterolateral ligament.

Advantageously, the superimposition of the current two-dimensional image I(t) and of the current localization zone L of the end of the piercing instrument 5 (FIG. 12b) can be displayed between these two superimpositions, by aligning FIGS. 12a, 12b and 12c.

Thus, by visualization in real time of the localization zone of the first orifice 11a of the bone tunnel 10 to be produced and of the localization zone of the second orifice 11b of the bone tunnel 10 to be produced, the surgeon can adaptively move the surgical piercing instrument 5 in order to avoid any intersection with anatomical structures to be preserved represented in the projections.

Advantageously, the programmable device 6 executes a first algorithm for calculating intersection of the localization zone of the first orifice 11a of the bone tunnel 10 with the projections of the anatomical structures present in the first projection $P_a$. The first algorithm for calculating intersection is performed on the basis of the knowledge of the real-time position in the space of the operating theatre of the preoperative three-dimensional model 9 (resulting from step E20) registered in real time on the peroperative three-dimensional model 7.

Likewise, advantageously, the programmable device 6 executes a second algorithm for calculating intersection of the localization zone of the second orifice 11b of the bone tunnel 10 with the projections of the anatomical structures present in the second projection $P_b$. The second algorithm for calculating intersection is performed on the basis of the knowledge of the real-time position in the space of the operating theatre of the preoperative three-dimensional model 9 (resulting from step E20) registered in real time on the peroperative three-dimensional model 7.

Advantageously, when the first algorithm for calculating intersection results in an intersection comprising a part of the projections of the anatomical structures present in the first projection $P_a$ (i.e. detection of an intersection between the current estimation of the localization zone of the first orifice and a part of the projections of the anatomical structures present in the first projection $P_a$) or when the second algorithm for calculating intersection results in an intersection comprising a part of the projections of the anatomical structures present in the second projection $P_b$ (i.e. detection of an intersection between the current estimation of the localization zone of the second orifice and a part of the projections of the anatomical structures present in the second projection $P_b$), the programmable device 6 can execute a display algorithm, on the first projection $P_a$, or respectively the second projection $P_b$, of an information message in order to warn the surgeon of the danger of damage for example.

Figure 13A:
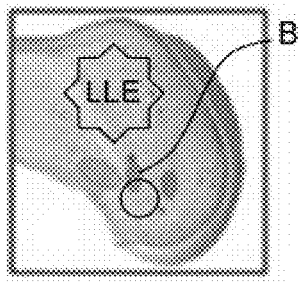
FIG. 13*a* represents a superimposition of an alert message on the first two-dimensional projection in FIG. 9.
Figure 13B:
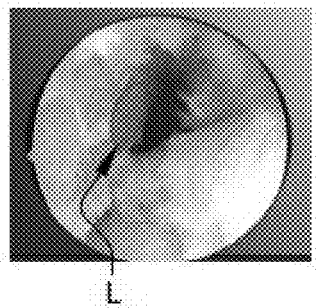
FIG. 13*b* is another example of superimposition of a peroperative two-dimensional image with a current localization zone of an end of a surgical piercing instrument such as the superimposition of FIG. 11, according to one or several embodiments.
Figure 13C:
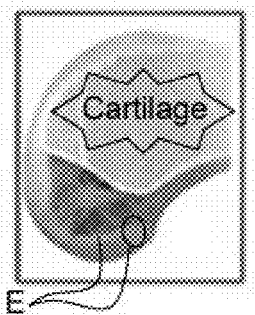
FIG. 13*c* represents a superimposition of another alert message on the other two-dimensional projection of FIG. 10 according to one or several embodiments.

FIGS. 13a and 13c show examples of such superimpositions (i.e. superimposition images). On FIG. 13a, the superimposition image further comprises the information message 'LLE' meaning that there is detected intersection of an orifice to be produced with the femoral insertion of the external lateral ligament B. On FIG. 13c, the superimposition image further comprises the information message 'cartilage' meaning that there is intersection between the second orifice 11b to be produced and the inferior cartilaginous boundary.

Advantageously, when the first algorithm for calculating intersection results in an intersection not comprising a noble anatomical structure of interest, and the second algorithm for calculating intersection results in an intersection not comprising noble anatomical structures of interest, the programmable device 6 can execute a display algorithm, on the first projection $P_a$, or respectively, the second projection $P_b$, of a positive message aimed at advising the surgeon that the positioning and the orientation of the surgical instrument 5 are reliable and that they can proceed with the piercing of the bone tunnel 10.

Figure 14:
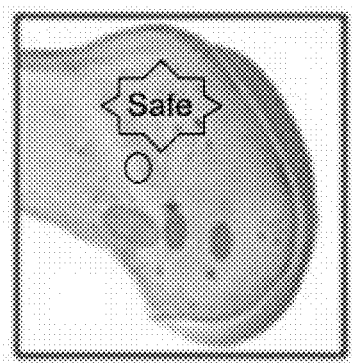
FIG. 14 represents a superimposition of a positive message for the production of a bone tunnel according to one or several embodiments.

FIG. 14 shows an example of such a superimposition. On FIG. 14, the information message 'Safe' means that the position and the orientation of the end of the surgical piercing instrument 5 are compatible with a secure piercing of the bone tunnel 10.

In another aspect of the invention, the real-time assistance system 1 allows also to assist the surgeon in the production of several bone tunnels during the same operation.

It is supposed here that a first bone tunnel 10a has been produced in the knee of the patient and that a second bone tunnel 10b must also be produced in the knee of the patient.

On the basis of the position and orientation $D_f(t_1)$ of the end of the surgical piercing instrument 5 that were used at the instant $t_1$ to produce the first bone tunnel, the programmable device 6 executes a calculation algorithm aimed at calculating a three-dimensional representation of the first bone tunnel 10a (already produced and present in the bone) as well as the localization of this representation in the superimposition S(t) (i.e. superimposition image calculated and displayed in real time) as follows.

The calculation algorithm is executed on the basis of the knowledge of the real-time position in the space of the operating theatre of the preoperative three-dimensional model 9 (resulting from step E20) registered in real time on the peroperative three-dimensional model 7, and on the basis of the knowledge of the real-time position in the space of the operating theatre of the surgical piercing instrument 5. The algorithm thus allows to record the trajectory of the surgical piercing instrument 5 when the latter penetrates and is moved inside a bone structure. The recorded trajectory can then be displayed in real time. The three-dimensional representation of the first bone tunnel 10a corresponds to the recorded trajectory.

For example, the three-dimensional representation of the first bone tunnel 10a can be displayed on the superimposition S(t). In another example, a two-dimensional view of the three-dimensional representation of the first bone tunnel 10a can be calculated and displayed in superimposition on one among the first projection $P_a$ and the second projection $P_b$.

It is supposed that at the current instant t, the surgeon is in the process of positioning the end of the piercing instrument 5 in order to produce the second bone tunnel 10b.

Advantageously, the programmable device 6 executes a display algorithm, on the first current projection $P_a$ and on the second current projection $P_b$, of the representation of the first bone tunnel 10a already produced.

In other words, the system is configured to generate a two-dimensional view of the three-dimensional representation of the first bone tunnel 10a already produced and to produce a superimposition image that comprises a superimposition of the first projection $P_a$. This two-dimensional view can be displayed (or rendered) on the superimposition image using a first pattern, for example a pattern in broken lines or a hatched pattern. In the same way, the system is configured to generate a two-dimensional view of the three-dimensional representation of the first bone tunnel 10a already produced and to produce a superimposition image that comprises a superimposition of the second projection $P_b$. This two-dimensional view can be displayed (or rendered) on the superimposition image using a second pattern, identical to or different from the first, for example a pattern in broken lines or a hatched pattern.

Figure 15:
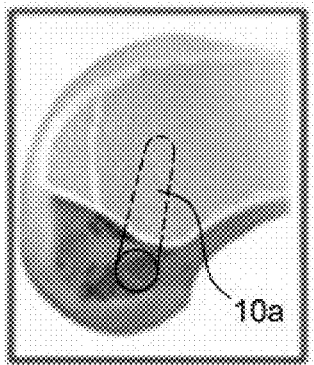
FIG. 15 represents a superimposition of a representation of a bone tunnel produced on a two-dimensional projection according to one or several embodiments.

FIG. 15 illustrates an example of such a display, where the two-dimensional view of the three-dimensional representation of the first bone tunnel 10a is represented in hatched (i.e. pattern).

In an alternative example, the representation of the first bone tunnel is displayed in the form of a digital hologram superimposed on the first current projection $P_a$, respectively the second current projection $P_b$. This enables the surgeon to have a vision in three-dimensions of their working space. For example, the surgeon can visualize the first current projection $P_a$ through augmented reality glasses, such as visualization glasses of a Hololens™ system.

In order to avoid intersections between the first bone tunnel 10a already produced and the second bone tunnel 10b to be produced, the programmable device 6 advantageously executes, apart from the first algorithm for calculating intersection and the second algorithm for calculating intersection, a third algorithm for calculating intersection between the trajectory of the second bone tunnel 10b to be produced that is calculated in real time from the position in the space of the operating theatre of the piercing instrument 5 and from the position in the space of the preoperative three-dimensional model 7 and the representation of the first bone tunnel 10a. Likewise, the programmable device 6 advantageously executes a fourth algorithm for calculating intersection between the trajectory of the second bone tunnel 10b to be produced and the representation of the first bone tunnel 10a.

Advantageously, when the third algorithm for calculating intersection results in a non-void intersection, i.e. comprising a part of the representation of the first bone tunnel 10a previously produced, or when the fourth algorithm for calculating intersection results in a non-void intersection, i.e. comprising a part of the representation of the first bone tunnel 10a previously produced, the programmable device 6 can execute an algorithm displaying, on the first projection $P_a$, or respectively, the second projection $P_b$, an information message in order to warn the surgeon of the risk of intersection with the first bone tunnel 10a already produced.

Advantageously, when the third algorithm for calculating intersection results in a void intersection, and the fourth algorithm for calculating intersection results in a void intersection, the programmable device 6 can execute an algorithm displaying, on the first projection $P_a$, or respectively, the second projection $P_b$, of a positive message aiming at warning the surgeon that the positioning and the orientation of the surgical instrument 5 are reliable and that they can proceed with the piercing of the second bone tunnel 10b.

Figure 16:
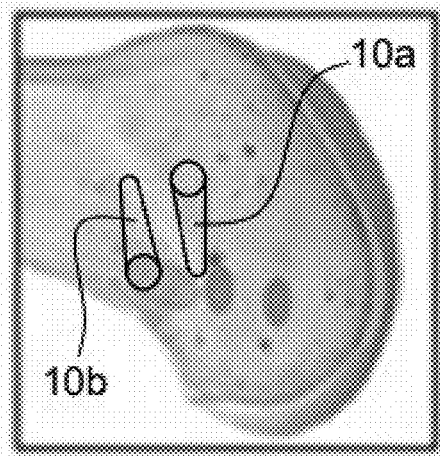
FIG. 16 represents a superimposition of a representation of a first bone tunnel already produced and of a predictive representation of a second bone tunnel to be produced during a same operation according to one or several embodiments.

FIG. 16 illustrates a projection among the first projection $P_a$ and the second projection $P_b$, on which there have been superimposed a two-dimensional view of the three-dimensional representation of the first bone tunnel 10a already produced and a two-dimensional view of the predicted three-dimensional representation of the second bone tunnel 10b to be produced corresponding to the current position and orientation of the end of the piercing instrument 5. Such an illustration of the superimposition allows to adjust the current position and orientation of the end of the piercing instrument 5 in order to avoid any interference between the first bone tunnel 10a already existing and the second bone tunnel 10b to be produced. If there is no intersection between the first bone tunnel 10a already produced and the trajectory of the second bone tunnel 10b to be produced, the two-dimensional view of the three-dimensional representation of the latter is displayed in totality, as on FIG. 16. If there is an intersection, an information message is displayed in place of the trajectory of the second bone tunnel 10b.

Another aspect of the invention relates to a method for real-time assistance in the production of at least one bone tunnel 10 by arthroscopy in a joint of a patient, comprising the following steps:

receiving, E100, a preoperative three-dimensional anatomical model 7 specific to the patient, said model comprising a representation of the joint of the patient and a representation of anatomical structures of interest, acquiring, E200, using an imaging device 2, a stream of peroperative two-dimensional images, said peroperative two-dimensional images comprising a portion of interest of the joint, and acquiring monitoring information of the current position and orientation $D_f(t)$ of the imaging device using the monitoring device 3, or alternatively, acquiring, using a measuring device, a cloud of points representative of the portion of interest of the joint, and acquiring monitoring information of the current position and orientation of said measuring device acquiring, E300, using a monitoring device 3 of a surgical piercing instrument 5, monitoring information of the position and orientation $I_P(t)$ of said surgical piercing instrument 5 during a manipulation of said surgical piercing instrument 5 by an operator, determining, E400, a peroperative partial three-dimensional anatomical model 9 from the stream of peroperative two-dimensional images (and from monitoring information of the current position and orientation $D_f(t)$ of the imaging device) or alternatively, from the cloud of points representative of the portion of interest of the joint obtained using the measuring device (and from monitoring information of the current position and orientation of the measuring device), registering, E500, the peroperative partial three-dimensional anatomical model 9 on the preoperative three-dimensional anatomical model 7;

calculating, E600, on the basis of a current peroperative two-dimensional image I(t) comprising the portion of interest of the joint:

a current zone of localization, in the current peroperative two-dimensional image I(t), of a piercing end of the surgical piercing instrument 5, a first projection comprising a current estimation of a zone of localization of a first orifice 11a of a bone tunnel 10 to be produced;

a second projection comprising a current estimation of a zone of localization of a second orifice 11b of the bone tunnel 10 to be produced.

Figure 17:
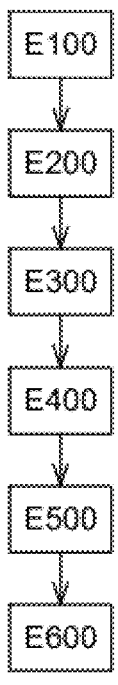
FIG. 17 is a flowchart of the steps implemented during a method for real-time assistance in the production by arthroscopy of at least one bone tunnel according to one or several embodiments.

The various steps of this method are illustrated on the flowchart of FIG. 17.

The invention claimed is:

1. A system for assisting with a production of at least one bone tunnel by arthroscopy in a joint of a patient using a surgical piercing instrument, the system comprising an imaging device or a measuring device, a monitoring device, a visualization unit and a programmable device, said programmable device adapted to:

obtain a preoperative three-dimensional anatomical model specific to the patient, said preoperative three-dimensional anatomical model comprising a representation of at least one portion of interest of the joint of the patient and a representation of anatomical structures of interest, acquire monitoring information of a current position and orientation of the surgical piercing instrument $I_P(t)$ during a manipulation of said surgical piercing instrument using the monitoring device;

determine a peroperative partial three-dimensional anatomical model comprising a representation of the at least one portion of interest of the joint, by:

acquiring, using the imaging device, a stream of peroperative two-dimensional images comprising said at least one portion of interest of the joint, and acquiring monitoring information of the current position and orientation $D_f(t)$ of the imaging device using the monitoring device; wherein said peroperative partial three-dimensional anatomical model is obtained from the stream of peroperative two-dimensional images and said monitoring information of the current position and orientation $D_I(t)$, or acquiring, using the measuring device, a cloud of points representative of the at least one portion of interest of the joint, and acquiring monitoring information of the current position and orientation of said measuring device; wherein said peroperative partial three-dimensional anatomical model is obtained from said cloud of points;

register the preoperative three-dimensional anatomical model on the peroperative partial three-dimensional anatomical model;

calculate, based on at least information obtained with the registering of the preoperative three-dimensional anatomical model, and of the current position and orientation $I_P(t)$ of the surgical piercing instrument:

a current zone L of localization, in a current peroperative two-dimensional image I(t), of a piercing end of the surgical piercing instrument, a first projection $P_A$ comprising a current estimation of a zone of localization of a first orifice of a bone tunnel to be produced, a second projection $P_B$ comprising a current estimation of a zone of localization of a second orifice of a bone tunnel to be produced, at least one of:

in the first projection $P_A$, first projections of a first part of the representation of the anatomical structures of interest during an operation phase, or in the second projection $P_B$, second projections of a second part of the representation of the anatomical structures of interest, and at least one of:

a first intersection between the current estimation of the zone of localization of the first orifice with the first projections of the first part of the representation of the anatomical structure of interest, or a second intersection between the current estimation of the zone of localization of the second orifice with the second projections of the second part of the representation of the anatomical structures of interest; and display on the visualization unit:

a superimposition of the current peroperative two-dimensional image I(t) and of the current zone L of localization of the piercing end of the surgical piercing instrument, a first superimposition of the first projection $P_A$ and of the first projections of the first part of the representation of the anatomical structures of interest, and a second superimposition of the second projection $P_B$ and of the second projections of the second part of the representation of the anatomical structures of interest.

2. The system according to claim 1, wherein the anatomical structures of interest comprise bone reliefs, cartilaginous boundaries, and tendinous or ligamentous structures.

3. The system according to claim 1, further adapted to, before obtaining the preoperative three-dimensional anatomical model, obtain and store a plurality of preoperative two-dimensional images comprising the portion of interest of the joint.

4. The system according to claim 1, further adapted, when the first intersection or the second intersection comprises a portion of the first projections of the first part of the representation of the anatomical structures of interest or a portion of the second projections of the second part of the representation of the anatomical structures of interest respectively, to display an information message on the first superimposition or the second superimposition respectively.

5. The system according to claim 1, further adapted to, after a production of a first bone tunnel in the joint of the patient, calculate a three-dimensional representation of the first bone tunnel and calculate, on the first projection $P_A$ and the second projection $P_B$, a current projection of a first and a second two-dimensional view of said three-dimensional representation of the first bone tunnel respectively.

6. The system according to claim 5, further adapted to display, on the first projection $P_A$, the first two-dimensional view and, on the second projection $P_B$, the second two-dimensional view.

7. The system according to claim 5, further adapted to calculate at least one of a first intersection between the current estimation of the zone of localization of the first orifice and the first two-dimensional view or a second intersection between the current estimation of the zone of localization of the second orifice and the second two-dimensional view.

8. The system according to claim 7, further adapted, when the first intersection or the second intersection comprises at least one portion of the first two-dimensional view or at least one portion of the second two-dimensional view respectively, to display an information message on the first superimposition or the second superimposition respectively.

9. A computer-implemented method for assisting with a production of at least one bone tunnel by arthroscopy in a joint of a patient using a surgical piercing instrument, said method comprising:

obtaining a preoperative three-dimensional anatomical model specific to the patient, said preoperative three-dimensional anatomical model comprising a representation of at least one portion of interest of the joint of the patient and a representation of anatomical structures of interest, acquiring monitoring information of a current position and orientation of the surgical piercing instrument $I_P(t)$ during a manipulation of said surgical piercing instrument using a monitoring device;

determining a peroperative partial three-dimensional anatomical model, comprising a representation of said at least one portion of interest of the joint, by:

acquiring, using an imaging device, a stream of peroperative two-dimensional images comprising said at least one portion of interest of the joint, and acquiring monitoring information of the current position and orientation $D_I(t)$ of the imaging device using the monitoring device; wherein said peroperative partial three-dimensional anatomical model is obtained from the stream of peroperative two-dimensional images and said monitoring information of the current position and orientation $D_I(t)$, or acquiring, using a measuring device, a cloud of points representative of the at least one portion of interest of the joint, and acquiring monitoring information of the current position and orientation of said measuring device; wherein said peroperative partial three-dimensional anatomical model is obtained from said cloud of points, registering the preoperative three-dimensional anatomical model on the peroperative partial three-dimensional anatomical model; and calculating, based at least on information obtained with the registering of the preoperative three-dimensional anatomical model, and of the current position and orientation $I_P(t)$ of the surgical piercing instrument:

a current zone L of localization, in a current peroperative two-dimensional image I(t), of a piercing end of the surgical piercing instrument, a first projection $P_A$ comprising a current estimation of a zone of localization of a first orifice of a bone tunnel to be produced, and a second projection $P_B$ comprising a current estimation of a zone of localization of a second orifice of a bone tunnel to be produced at least one of:

in the first projection $P_A$, first projections of a first part of the representation of the anatomical structures of interest during an operation phase, or in the second projection $P_B$, second projections of a second part of the representation of the anatomical structures of interest, and at least one of:

a first intersection between the current estimation of the zone of localization of the first orifice with the first projections of the first part of the representation of the anatomical structure of interest, or a second intersection between the current estimation of the zone of localization of the second orifice with the second projections of the second part of the representation of the anatomical structures of interest; and displaying on a visualization unit:

a superimposition of the current peroperative two-dimensional image I(t) and of the current zone L of localization of the piercing end of the surgical piercing instrument, a first superimposition of the first projection $P_A$ and of the first projections of the first part of the representation of the anatomical structures of interest, and a second superimposition of the second projection $P_B$ and of the second projections of the second part of the representation of the anatomical structures of interest.

10. A non-transitory computer-readable medium on which a computer program product comprising instructions to execute the steps of the method according to claim 9 is recorded.

11. A computer program product including instructions for implementing the method of claim 9, when the computer program product is executed by a processor.

12. The system of claim 1, wherein the measuring device is mounted on a robotic arm.

13. The system of claim 1, wherein acquiring monitoring information of the current position and orientation of the surgical piercing instrument $I_P(t)$ and the current position and orientation $D_I(t)$ of the imaging device is performed at least in part by triangulation.

14. The system of claim 1, wherein the peroperative two-dimensional images of the stream of peroperative two-dimensional images are monocular images.

15. The system of claim 1, wherein the peroperative partial three-dimensional anatomical model obtained from the stream of the peroperative two-dimensional images is obtained in substantially real time.

* * * * *